US00PP24536P2

(12) United States Plant Patent
Moore

(10) Patent No.: US PP24,536 P2
(45) Date of Patent: Jun. 10, 2014

(54) ***PHILADELPHUS* PLANT NAMED 'DAINTY LADY'**

(50) Latin Name: *Philadelphus microphyllus×delavayi var. calvesscens*
Varietal Denomination: Dainty Lady

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 77 days.

(21) Appl. No.: 13/573,742

(22) Filed: Oct. 4, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Penny J. Aguirre

(57) ABSTRACT

A new cultivar of *Philadephus*, 'Dainty Lady', characterized by its upright, narrowly spreading plant habit with suitability for growing in small gardens, its leaves that are narrow in shape and are tinged with maroon on the young growth in spring of the terminal shoots, its slender stems that on mature plants (2 years in age) turn brown to mahogany in color in winter and provides interest when not in flower, its highly fragrant flowers with calyces that are green/maroon in color, and its ability to grow under a wide range of soil conditions.

2 Drawing Sheets

Botanical classification: *Philadelphus microphyllus×delavayi* var. *calvesscens*.

Variety denomination: 'Dainty Lady'.

BACKGROUND OF THE INVENTION

The present invention relates to a new and distinct cultivar of *Philadelphus*, botanically a hybrid between *microphyllus× delavayi* var. *calvesscens* and will be referred to hereafter by its cultivar name, 'Dainty Lady'. 'Dainty Lady' is a new herbaceous shrub grown for use as a landscape plant.

The new cultivar of *Philadelphus* is a selection from a breeding program conducted by the Inventor in Longstock Hampshire, United Kingdom with the objective of creating a new cultivar of *Philadelphus* with unique characteristics and suitability for small gardens.

The new variety of *Philadelphus*, 'Dainty Lady', arose from a cross made in 1995 between an unnamed plant of *Philadelphus microphyllus* as the female parent and an unnamed plant of *Philadelphus delavayi* var. *calvescens* as the male parent. 'Dainty Lady' was selected as a single unique plant from the resulting seedling of the above cross in 1998.

Asexual reproduction of the new cultivar was first accomplished by softwood cuttings by the inventor in May in Stockbridge, Hampshire, United Kingdom in 2000. The characteristics of this cultivar have been determined to be stable and are reproduced true to type in successive generations.

SUMMARY OF THE INVENTION

The following traits have been repeatedly observed and represent the characteristics of the new cultivar as grown outdoors in Stockbridge, Hampshire, United Kingdom. These attributes in combination distinguish 'Dainty Lady' as a unique cultivar of *Philadelphus*.

1. 'Dainty Lady' exhibits an upright, narrowly spreading plant habit with suitability for growing in small gardens.

2. 'Dainty Lady' exhibits leaves that are narrow in shape and are tinged with maroon on the young growth in spring of the terminal shoots.
3. 'Dainty Lady' exhibits slender stems that on mature plants (2 years in age) turn brown to mahogany in color in winter and provides interest when not in flower.
4. 'Dainty Lady' exhibits flowers with calyces that are green/maroon in color.
5. 'Dainty Lady' exhibits flowers that are strongly fragrant.
6. 'Dainty Lady' grows in a wide range of soil conditions.

The unnamed plant of *Philadelphus microphyllus*, the seed parent of 'Dainty Lady', differs from 'Dainty Lady' in having a more twiggy, open habit and in having a larger plant size. The unnamed plant of *Philadelphus delavayi* var *calvescens*, the pollen parent of 'Dainty Lady', differs from 'Dainty Lady' in having a larger plant size, a more open plant habit, and larger leaves that are grey in color and tomentose on the lower surface. 'Dainty Lady' can be most closely compared to the cultivars 'Silberregen' (not patented) and *P. microphyllus* 'June Bride'. 'Silberregen' is similar to 'Dainty Lady' in having a dense small plant habit, and small pointed leaves. 'Silberregen' differs from 'Dainty Lady' in having a mounded and arching plant habit. 'June Bride' is similar to 'Dainty Lady' in having small leaves, but differs from 'Dainty Lady' in being shorter in height and wider in spread.

BRIEF DESCRIPTION OF THE DRAWING

The accompanying colored photographs illustrate the overall appearance and distinct characteristics of the new *Philadelphus*. The plants in the photographs were taken of a plant 18 months in age as grown outdoors in a 19-cm container in Boskoop, The Netherlands.

The photograph in FIG. 1 provides a side view of a plant of 'Dainty Lady' in bloom.

Figure 1:
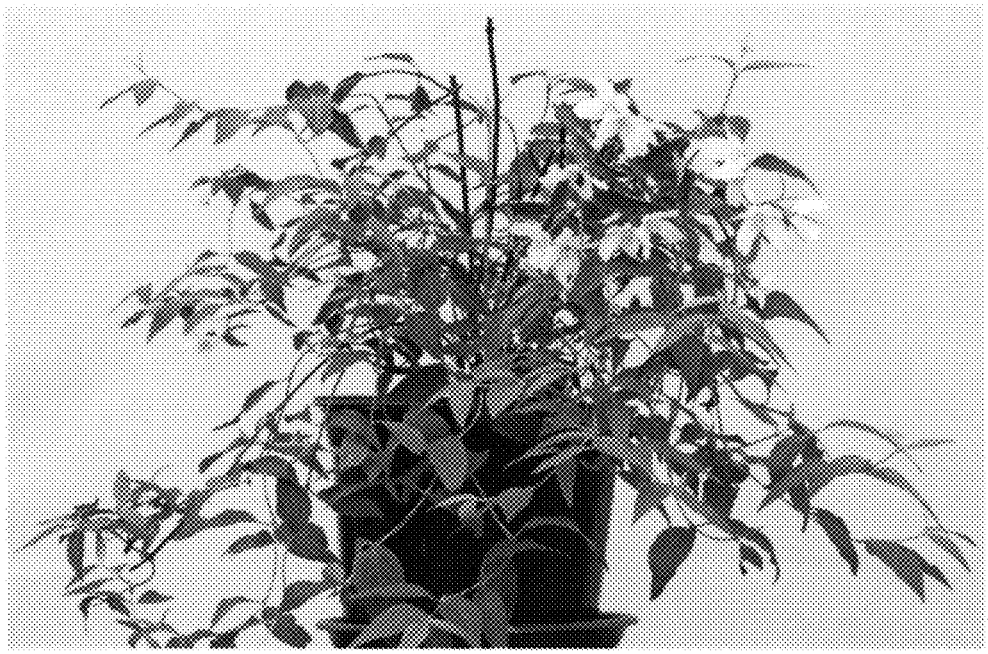
Figure 2:
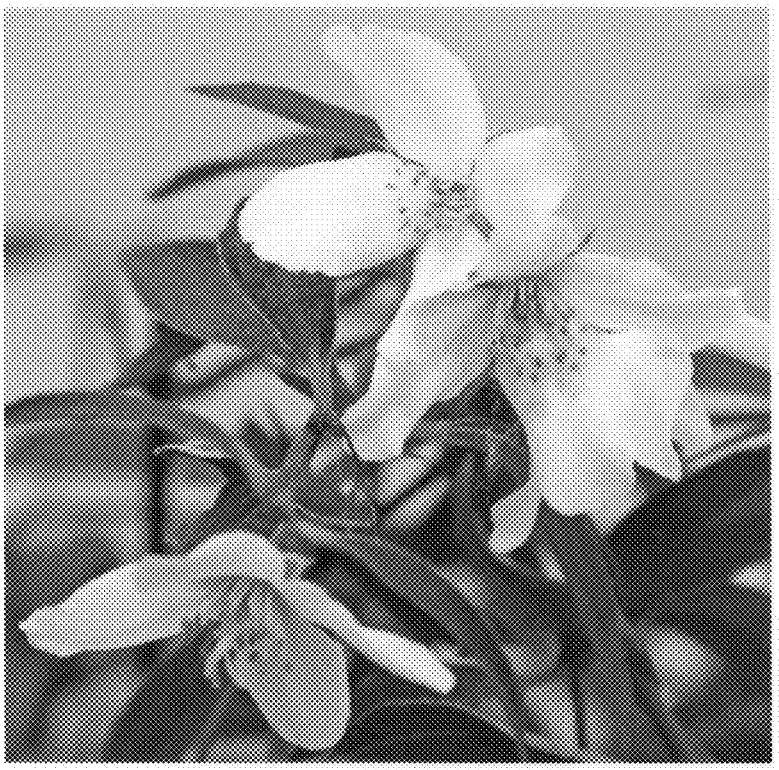

The photograph in FIG. 2 provides a close-up view of the flowers of 'Dainty Lady'.

Figure 3:
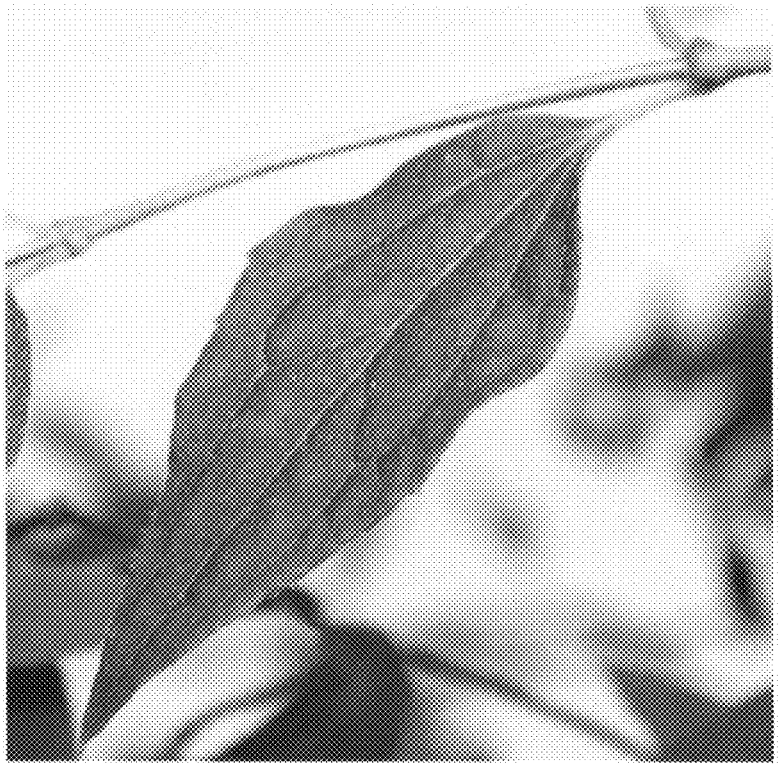

The photograph in FIG. 3 provides a close-up view of the foliage of 'Dainty Lady'. The colors in the photograph are as close as possible with the digital photography techniques available, the color values cited in the detailed botanical description accurately describe the colors of the new *Philadelphus.*

DETAILED BOTANICAL DESCRIPTION

The following is a detailed description of 18 month-old plants of the new cultivar as grown outdoors in 19-cm containers in Boskoop, the Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—From June to early July in the United Kingdom.

*Plant habit.*—Upright and narrowly spreading.

*Height and spread.*—Reaches about 25 cm in height and about 53 cm in diameter as an 18 month plant and about 2.5 m in height and 1.5 m in width when grown in the landscape (with flowering branches pruned each year).

*Cold hardiness.*—At least in U.S.D.A. Zone 5.

*Diseases and pests.*—No susceptibility or resistance to diseases or pests has been observed for 'Dainty Lady'.

*Propagation.*—Softwood stem cuttings.

*Growth rate.*—Moderate.

Stem description:

*Shape.*—Rounded.

*Stem color.*—A color between 147D and 148C, older bark 175A.

*Stem size.*—Average of 26.6 cm in length and 2 mm in diameter.

*Stem surface.*—Slightly sheen and covered with soft pubescent short hairs, 0.5 mm in length and 157A in color on young shoots and 164D on older stems.

*Internode length.*—An average of 3.6 cm.

*Branching habit.*—Free branching.

Foliage description:

*Leaf shape.*—Ovate to narrow ovate.

*Leaf division.*—Single.

*Leaf base.*—Short attenuate.

*Leaf apex.*—Acute.

*Leaf venation.*—Pinnate, upper surface 144A in color, lower surface 148C in color.

*Leaf margins.*—Entire to slightly toothed, when toothed and average of 6 small teeth are placed on the upper half of the leaf blade.

*Leaf arrangement.*—Opposite.

*Leaf attachment.*—Petiolate.

*Leaf surface.*—Slightly rugose and rough to the touch due to being moderately covered with short strigose hairs, average of 0.75 mm in length and 161D in color on upper and lower surface.

*Leaf size.*—Average of 4.6 cm in length and 1.9 cm in width.

*Leaf color.*—Young leaves upper surface; 138A with a tint of 183B when emerging in spring, young leaves lower surface; 138B to 138C, mature leaves upper surface; N137C, mature leaves lower surface; 191A.

*Petioles.*—Average of 0.7 cm in length, 1 mm in width and 144B in color.

Inflorescence description:

*Inflorescence type.*—Single flowers, most typically in pairs.

*Inflorescence size.*—Average of 3.6 cm in length (including peduncle) and 5.4 cm in width.

*Lastingness of inflorescence.*—About 3 weeks.

*Flower buds.*—Elliptic in shape, up to 1.3 cm in length and 6 mm in width and NN155A in color.

*Flower fragrance.*—Very strong and pleasant.

*Flower quantity.*—About 16 per lateral stem.

*Flower aspect.*—Outward to slightly drooping.

*Flower type.*—Rotate corolla above an elongated calyx.

*Flower size.*—Average of 3.5 cm in diameter and 1.8 cm in depth.

*Calyx.*—Rotate and cruciform in shape, average of 0.3 cm in length and 1.8 cm in width.

*Sepals.*—Average of 4, rotate and cruciform arrangement, ovate to elliptic in shape, surface is dull, 0.8 cm in length and 0.3 cm in width, margins entire and covered in softly pubescent very short hairs, average length of 0.2 mm and 157D in color, acute apex and fused base enclosing the ovary, color: immature upper surface; 143B, immature lower surface; 144A, mature upper and lower surface; 144A and suffused with 183A.

*Petals.*—4, nearly oblong in shape, un-fused, both surfaces smooth and dull, entire margins slightly revolute, rounded base, emarginate apex, about 1.8 cm in length and 1.1 cm in width, color: upper surface when opening; NN155B to NN155C, lower surface when opening; NN155B, upper and lower surfaces when fully opened; NN155C.

*Peduncle.*—Strong, an average of 1.1 cm in length and 0.1 cm in diameter, terminal peduncles straight on top of lateral branches (=0°), axillary peduncles in an average angle of 30° to lateral branches and 174A in color.

*Pedicels.*—Strong, an average length of 1.2 cm in length and 0.1 cm in diameter, average angle of 30° to lateral branch and 144B in color.

Reproductive organs:

*Gynoecium.*—1 pistil about 0.8 cm in length, style is 150D blending to 145D at the base in color, about 0.6 cm in length, stigma is three-parted and linear and 150D in color, ovary is 143C in color.

*Androecium.*—Average of 32 stamens, filaments are 0.7 cm in length, anthers are 161A in color, basifixed and oblong in shape, about 0.7 cm in length and width, pollen is low to moderate quantity and 11A in color.

*Fruit and seed.*—No fruit or seed observed to date.

It is claimed:

1. A new and distinct cultivar of *Philadelphus* plant named 'Dainty Lady' as herein illustrated and described.

* * * * *